Dec. 16, 1947. R. G. BAXTER Plant Pat. 770
SAINTPAULIA PLANT
Filed Jan. 16, 1947
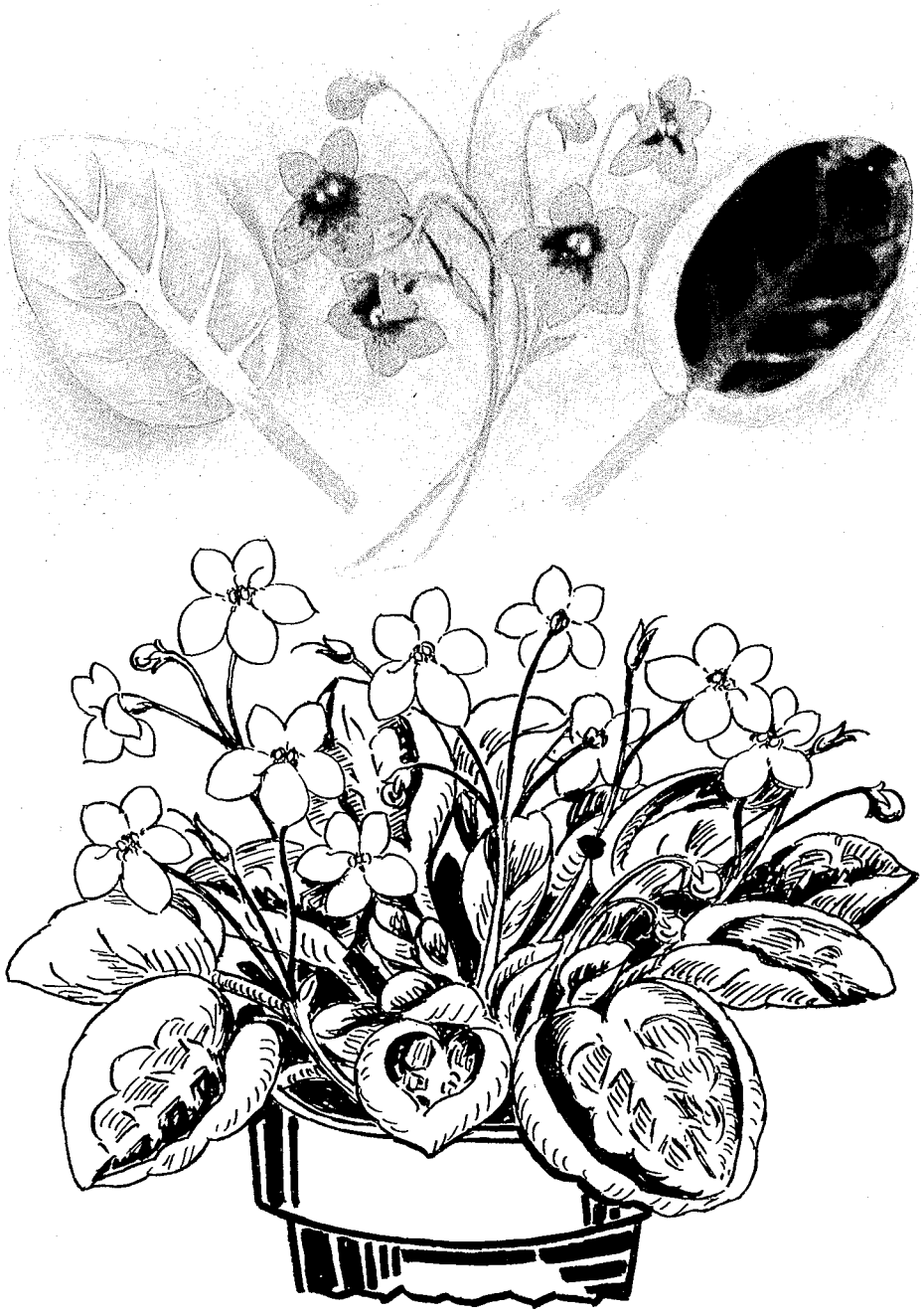
WITNESS
Addison E. Avery
INVENTOR
Roy G. Baxter,
Kummler Kummler & Davis,
ATTYS.

Patented Dec. 16, 1947

Plant Pat. 770

UNITED STATES PATENT OFFICE

770

SAINTPAULIA PLANT

Roy G. Baxter, Youngstown, Ohio

Application January 16, 1947, Serial No. 722,332

1 Claim. (Cl. 47—60)

My present discovery is a new and distinct variety of *Saintpaulia ionantha* grandiflora (Hort.) plant, herein described and illustrated. It is a cross between "Blue Boy" and "Bi-Color," which resulted from repeated crossings since September 1944. This new variety has been asexually reproduced by cuttings and its characteristics appear to be permanently fixed.

The novelty of this new variety resides primarily in the uniform coloring of the blooms, their large size, the slight cup-shape of the two upper petals, and the conspicuous form and coloring of the leaves.

The accompanying illustration shows above, in full color, a cluster of the flowers and leaves; and below, a pen and ink sketch of a single potted plant as a whole.

Referring to the novel characteristics of this new variety, when the buds first form only five greenish lavender colored sepals show with one long lavender colored style protruding. As they mature a purplish colored ball forms between the sepals, covering this style. These two forms of buds on one plant distinctively contrast with the hepatica colored flowers and vari-colored leaves of the plant. There is a large number of buds in both these stages on a single plant.

Another distinctive novelty of this new variety is the form and contrasting colors of the large green leaves. All of the leaves have upwardly and broadly inwardly curved margins, showing a decided border roll of such a light shade of green that it is almost white in comparison with the dark green color of the upper side of the leaf. There is a small spot of cream color where the petiole joins the base of the leaf, and the backs of the leaves are deeply ribbed and shaded between the vein ribs in tones of violet-pink which covers most of the back surface of the young leaves and fades into the whitish color in the older leaves. The leaves are heavily veined and the intervening web portions bulge in local areas in blister-like curvature.

The young leaves in the middle of the clump are upstanding; they are convolute in their early development and their margins begin to curl symmetrically as they expand and grow to maturity. The young leaves have a decided violet shade of color spreading to their edges and this recedes from the margins inward as the leaf develops. As the leaves enlarge, this violet shading gradually recedes and fades to a less conspicuous shade and concentrates along the rib. As the leaves age the upper side becomes very shiny in appearance. Thus the plant as a whole is most conspicuous in its assortment of colors.

The following is an itemized description in schedule form of the new variety:

Parentage: Seedling:
- *Seed parent.*—"Blue Boy."
- *Pollen parent.*—"Bi-Color."

Classification, botanic: *Saintpaulia ionantha* grandiflora (Hort.).

*Flower*

Blooming habit: Recurrent.
- *Bud.*—*Size*—⅛ inch to ¼ inch. *Form*—gamesepalous. *Color*—greenish lavender. *Sepals*—number, usually 5. Shape, pointed. *Calyx*—size, $\frac{3}{16}$ inch to ¼ inch; 5 lobed.
- *Bloom.*—*Size*—1⅛ inches to 1¼ inches. *Form*—short tubed, five-lobed corolla. *Color*—hepatica. *Borne*—cymose inflorescence. *Stems*—slender; length: 1 inch to 1¼ inches, peduncle joined to 3 inch to 4 inch stalk of cyme. *Discoloration*—none. *Texture*—silky. *Affected by wet or hot weather*—not noticeably. *Persistence*—deciduous. *Disease resistance*—no common diseases. *Lasting quality*—good; on plant 1 week to 10 days.

Genital organs:
- *Stamens, anthers.*—2-celled; length $1\frac{1}{16}$ inches; number, 2.
- *Color.*—Yellow.
- *Arrangement.*—Opposite and attached by filament to corolla tube.
- *Pollen.*—Yellow.
- *Styles.*—Number, one; length, ½ inch.
- *Ovaries.*—Superior.

Fruit:
- *Shape.*—2-valved oblong capsule.
- *Color at maturity.*—Green, changing to brown.

*Plant*

Form: Sub-acaulescent.
- *Height.*—6 inches.
- *Foliage.*—*Quantity*—12 to 28 in rosette. *Size of leaf*—up to 2½ inches long to two inches wide. *Texture*—pubescent. *Shape*—ovate, spoon-shaped.

The color designations according to "A Dictionary of Color by Maerz and Paul," are as follows:

| | Plate | Letter | No. |
|---|---|---|---|
| Main flower color | 42 | K | 8 |
| Style | 42 | K | 8 |
| Stamens | 9 | L | 5 |
| Body of leaf (upper side) | 22 | L | 9 |
| Back of leaf and outside rolled rim | 17 | B | 2 |
| Pink areas along large rib on back of leaf | 4 | G | 7 |
| Flower stem | 7 | J | 7 |

This new variety of Saintpaulia plant is in most respects distinctively different from its parent varieties and has many features tending to give it decorative and commercial value.

Having thus disclosed my invention, I claim:

A new and distinct variety of Saintpaulia plant, substantially as described, and characterized particularly by the distinctive hepatica purple coloring and abundance of flowers, the coloring of the leaves with green upper surface and lower whitish surface variegated with violet-pink most pronounced in the young leaves and almost disappearing in the large leaves, and the form of the mature leaves with wide upwardly and inwardly rolled margins.

ROY G. BAXTER.